United States Patent
Schecter

(10) Patent No.: US 7,426,412 B1
(45) Date of Patent: Sep. 16, 2008

(54) EVOKED POTENTIAL AND IMPEDANCE BASED DETERMINATION OF DIAPHRAGMATIC STIMULATION

(75) Inventor: Stuart O. Schecter, Great Neck, NY (US)

(73) Assignee: Pacesetter, Inc., Sylmar, CA (US)

( * ) Notice: Subject to any disclaimer, the term of this patent is extended or adjusted under 35 U.S.C. 154(b) by 342 days.

(21) Appl. No.: 11/249,660

(22) Filed: Oct. 12, 2005

Related U.S. Application Data

(60) Provisional application No. 60/618,516, filed on Oct. 13, 2004, provisional application No. 60/627,859, filed on Nov. 15, 2004.

(51) Int. Cl.
*A61N 1/08* (2006.01)

(52) U.S. Cl. ............... 607/20; 607/9; 607/17; 600/509; 600/513; 600/484

(58) Field of Classification Search ............ 607/11, 607/17, 20, 25–28
See application file for complete search history.

(56) References Cited

U.S. PATENT DOCUMENTS

| 5,913,308 A * | 6/1999 | Forbes et al. ............... 600/513 |
| 7,225,021 B1 * | 5/2007 | Park et al. ................. 607/18 |
| 2003/0065365 A1 * | 4/2003 | Zhu et al. .................. 607/17 |

* cited by examiner

*Primary Examiner*—Carl H. Layno
*Assistant Examiner*—Eugene T Wu

(57) ABSTRACT

A system and method are described for automatically detecting diaphragmatic stimulation (DS) based on evoked response signals, electrogram data and/or thoracic impedance measurements. In addition, several optional modalities are described to circumvent this problem and alleviate symptoms related to DS while preserving LV pacing.

18 Claims, 4 Drawing Sheets

EVOKED POTENTIAL AND IMPEDANCE BASED DETERMINATION OF DIAPHRAGMATIC STIMULATION

CROSS-REFERENCE TO RELATED APPLICATIONS

This application claims the benefit of U.S. Provisional Applications Ser. No. 60/618,516, filed Oct. 13, 2004, and Ser. No. 60/627,859, filed Nov. 15, 2004.

FIELD OF THE INVENTION

The invention relates to implantable cardiac stimulation devices and, more particularly, to such devices that are capable of delivering left ventricular pacing pulses and of detecting diaphragmatic stimulation resulting from delivery of the left ventricular pacing pulses.

BACKGROUND OF THE INVENTION

Current Cardiac Resynchronization Therapy ("CRT") pacing systems utilize left ventricular ("LV") leads for pacing the left ventricle and reducing inter-ventricular and intra-ventricular dysynchrony, which leads to improved cardiac output, reduction of dysynchrony, reverse remodeling, less heart failure symptomatology and potentially improved longevity.

In some situations, pacing with an LV lead may cause diaphragmatic stimulation ("DS"). DS causes a patient to have hiccups that occur either intermittently or, in severe cases, every time a pacing impulse is delivered and often requires deactivation of the LV pacing electrode. DS is uncomfortable to the patient and will often require an office or emergency room visit, thereby consuming valuable resources and being an inconvenience for the patient.

Deactivation of LV pacing may lead to worsening of congestive heart failure symptoms, and therefore is not an ideal or even viable option. Often a reduction in current delivery will reduce the frequency of DS, but a method of automatically detecting and troubleshooting DS is needed.

SUMMARY

What is described herein is a system and method for automatically detecting DS based on evoked response signals and/or thoracic impedance data. In addition, several optional modalities are described to overcome DS in the event it is detected, while preserving LV pacing.

BRIEF DESCRIPTION OF THE FIGURES

Further features and advantages of the invention may be more readily understood by reference to the following description, taken in conjunction with the accompanying drawings, in which.

DETAILED DESCRIPTION

The invention is described below, with reference to detailed illustrative embodiments. It will be apparent that the invention may be embodied in a wide variety of forms, some of which may be quite different from those of the disclosed embodiments. Consequently, the specific structural and functional details disclosed herein are merely representative and do not limit the scope of the invention. As is well known in the art, pacing stimuli delivered to cardiac tissue results in local electrical phenomenon, called evoked potentials or the evoked response, which can be detected by pacing electrodes. Such evoked potentials are often utilized for determining if capture of myocardial tissue has occurred (capture verification) and can further serve to guide automatic adjustment of pacing stimuli (capture threshold) in some implanted pacing systems.

Figure 1:
FIG. 1 depicts evoked potentials for normal LV capture.
Figure 2:
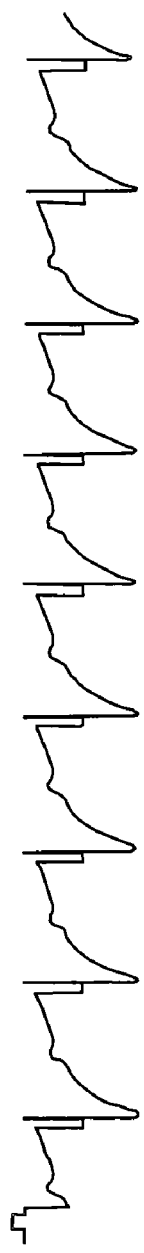
FIG. 2 depicts evoked potentials where diaphragm stimulation exists.

The characteristics of evoked potentials vary under different circumstances. After implantation of a screw-in lead, such signals may demonstrate changes associated with an injury pattern. These stabilize and reach a steady state within a very short duration after lead implantation. One way in which the evoked potentials vary is based on whether DS exists or not. Evoked potentials during LV pacing without any DS (FIG. 1) will differ from those detected when DS is present (FIG. 2). Such evoked potentials will also have different characteristics when non-capture is present and DS is occurring. As such these signals may be utilized for automatic identification of DS and/or capture. These signals may be analyzed with either unipolar or bipolar configurations.

Figure 3:
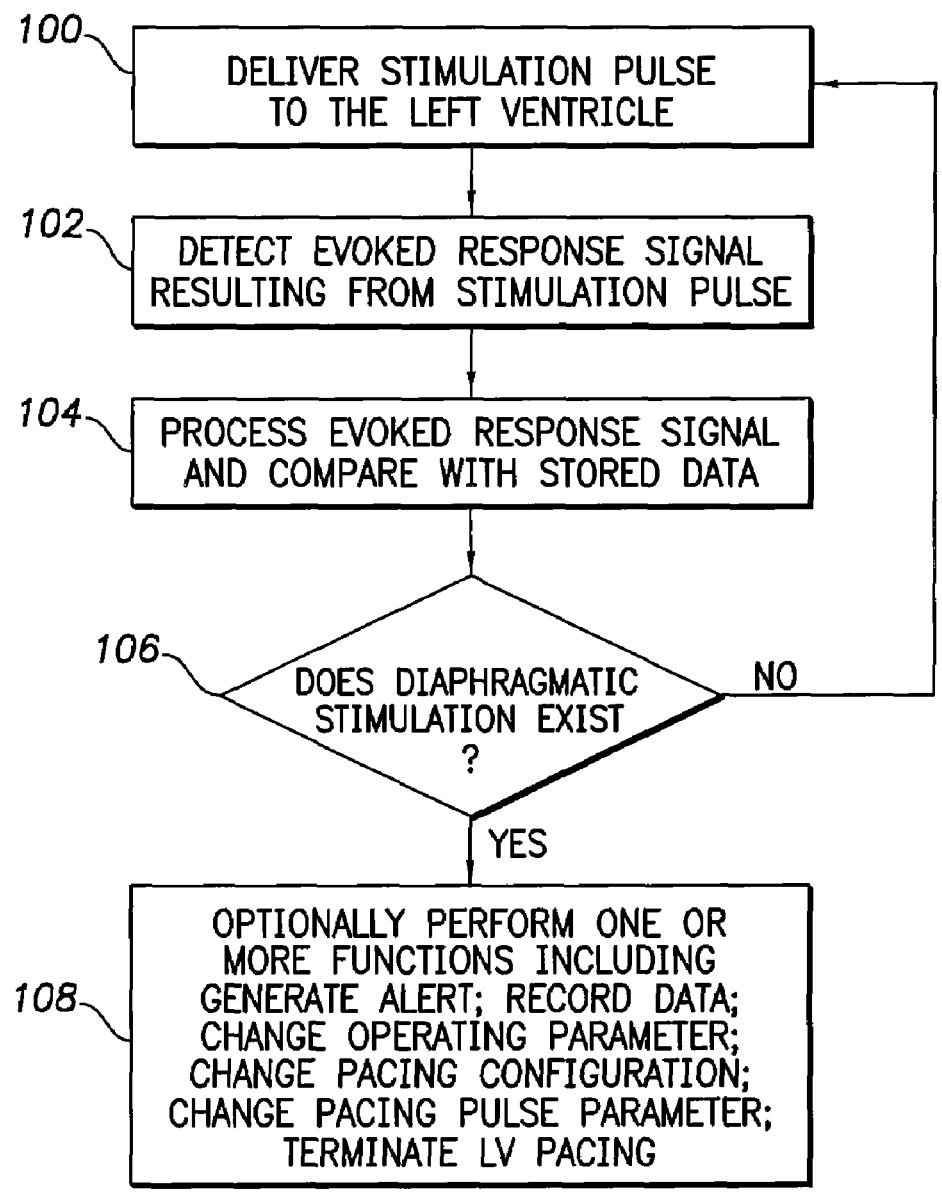
FIG. 3 depicts a flow diagram according to one illustrative embodiment.

Referring now to FIG. 3, a flowchart of one illustrative embodiment is shown. According to the illustrative embodiment, at step 100 the implanted system delivers a pacing pulse to the left side of the heart via the LV lead. The pacing pulse may be delivered via a unipolar or bipolar configuration. At step 102, the resulting evoked response is sensed by a pair of implanted electrodes. In one embodiment, the same electrodes used to deliver the pacing pulse sense the evoked response. In alternate embodiments, different electrodes on the LV lead, or far-field electrodes, or a unipolar configuration using the implanted device's housing as the return electrode may be used to detect the evoked response.

At step 104, the sensed signal is processed and analyzed to determine if the signal is indicative of DS. In one embodiment, the evoked response signal is compared to one or more templates stored by the implanted device. For example, the implanted device may store a template of an evoked response signal resulting from the combination of capture and DS. If the evoked response sufficiently matches the template, then the implanted device verifies capture of the heart tissue, and also determines that DS exists.

In another embodiment, the implanted device stores a plurality of different templates, corresponding to a plurality of the following scenarios: capture without DS, capture with DS, non-capture without DS, and non-capture with DS. The evoked response is then compared with the plurality of templates to determine the result of the pacing pulse. In this embodiment, the templates can be used to both detect diaphragmatic stimulation and verify capture of the left ventricle.

In still another embodiment, the implanted device may process the evoked response signal to determine one or more characteristics of the signal, and compare those one or more characteristics with stored values to determine if DS exists. For example, the amplitude of the evoked response signal, maximum slope (e.g., derivative of the evoked response signal), integral of the evoked response signal, or other such values can be determined and compared with stored values to determine if DS exists.

At query block 106, the implanted device determines if DS exists. If so, operation optionally proceeds to step 108, and one or more actions may be taken in response to that determination. For example, an alert signal may be generated and transmitted to an external device, such as a transtelephonic monitoring system, holter monitor, or other device external to the patient and within telemetric range of the implanted device. Alternately, the implanted device may record the data, change a pacing pulse parameter, change the pacing configuration, or perform other such actions, as is described in more detail below.

It will be understood by those skilled in the art that the optional actions in step 108 can be carried out only after detecting DS a plurality of times. For example, operation could proceed to step 108 only after detecting DS in a number of consecutive cycles, or after a predetermined number of DS events have been detected, or where DS events have occurred in X of the last Y cycles, where X and Y are positive integers.

In addition, the algorithm shown in FIG. 3 may be performed on a beat-by-beat basis or, alternatively, may be performed intermittently, for example, run for a predetermined period of time (e.g., one minute) once per day, once per week, or the like.

While in one illustrative embodiment the system relies solely on evoked response signals to detect DS, the perceptible characteristics of DS can also extend to the electrogram (EGM) signals obtained from the implanted leads (i.e., the signals resulting from intrinsic cardiac activity). A combination of evoked potential and electrogram signal characteristics/morphology can identify DS in the system described.

In yet another illustrative embodiment, impedance data related to respiration, Z(t)r, can be utilized as input data to the system as specific abnormalities in such impedance data will be found under conditions of spasmodic higher amplitude tidal volumes and/or higher frequency respirations. Thoracic impedance measurements are commonly used to determine respiratory rate and direct programming of rate responsive pacing. Patients implanted with such rate responsive devices who are exercising have increases in tidal volume and respiratory rate and thus, increased minute ventilation. These changes occur as a result of alterations in thoracic lung volume and corresponding changes in thoracic impedance detected by the implanted device and are well known by those experienced in the art. In a preferred embodiment, thoracic impedance parameters are implemented to detect DS Additionally, the detected respiratory rate will be increased as a result of DS which can occur with each pacing impulse. In presence of DS, increases in tidal volume will increase peak thoracic impedance values and cause large, relatively high frequency fluctuations in the respiratory component of thoracic impedance waveforms. By way of example, a patient that has DS may have contraction of the diaphragmatic muscle at the programmed base rate of the implanted device. This increased respiratory frequency is detected by electrodes that traverse the lung parenchyma and are detected by the CRT device. In one embodiment, the electrode pair used for detecting the affect of DS on thoracic impedance will traverse the left hemithorax, though any combination of electrodes can be used in the device.

Figure 4:
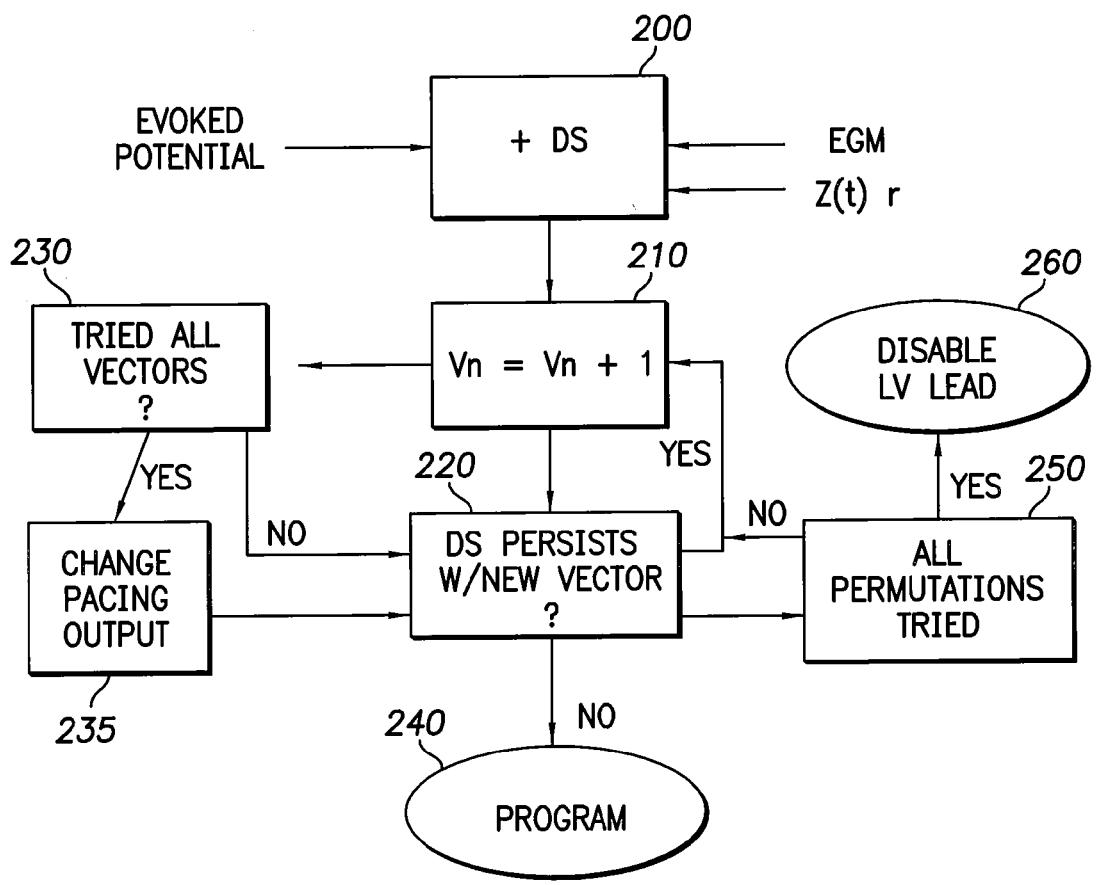
FIG. 4 depicts a flow diagram according to another illustrative embodiment.

In the event where DS is identified by evoked response, EGM and/or impedance data, a number of changes in the pacing configuration and/or stimulation strength can occur. FIG. 4 illustrates an algorithm designed to modify pacing characteristics when DS has been identified based on one or more of the evoked potential, EGM signal, and impedance signal as inputs to block 200. Upon DS identification, the system will change the pacing stimulation vector, $V_n$ (step 210). For example, the pacing configuration for LV pacing can initially be bipolar using tip and ring electrodes on the LV lead, and the new pacing stimulation vector may be configured to use the right ventricular coil on an RV lead as an alternate positive electrode. In this example the LV tip or ring may act as the negative electrode. Various different pacing configurations or vectors may be utilized in an attempt to eliminate DS, including using electrode in the right atrium, SVC, the device housing as a return electrode, and the like.

Changing the vector, Vn, to the next vector programmed, Vn+1, at step 210 is preferably carried out according to a predefined order of pacing vectors, which is either a default list or may be programmed by an operator. If DS is still present at step 220, operation may loop back to step 210 and a different vector may be used and so forth. Multiple vectors may be tested until the evoked potential, thoracic impedance DS parameter and/or electrogram characteristics do not suggest DS is present, at which point operation proceeds to step 240 and the device programs the new vector as the one for delivering LV pacing pulses. If all the vectors tested result in DS at step 230, changes in the pacing stimulus strength (lower current and/or pulse width) can be made at step 235 and one or more vectors can be re-tested until a suitable vector and pacing stimulus strength is found that maintains capture. If at step 250 no vector can be found to have adequate capture thresholds without DS, LV pacing may optionally be disabled at step 260.

It will be apparent to those skilled in the art that the order of steps shown in FIG. 4 can be varied. For example, after a vector results in DS, one or more of the pacing pulse parameters can be varied (step 235) and the same vector tested again with the new pacing pulse parameters. Then, if DS still exists, operation may return to step 210 for selection of a new vector.

Thus, the system is designed to identify DS using evoked potential, thoracic impedance measurements and/or electrogram characteristics, and automatically change pacing vector, pacing output, or eliminate LV pacing altogether if necessary. The order of preference for the pacing vectors may be programmed as a default or by the implanter and can be determined based on data representative of any cardiac performance parameter whether determined internally within the device (e.g. impedance signal data) or externally (e.g. ultrasound derived data). The decision of such an order and which permutations of pacing output and vector are utilized in the algorithm may be programmable manually or automatically (see below).

Figure 5:
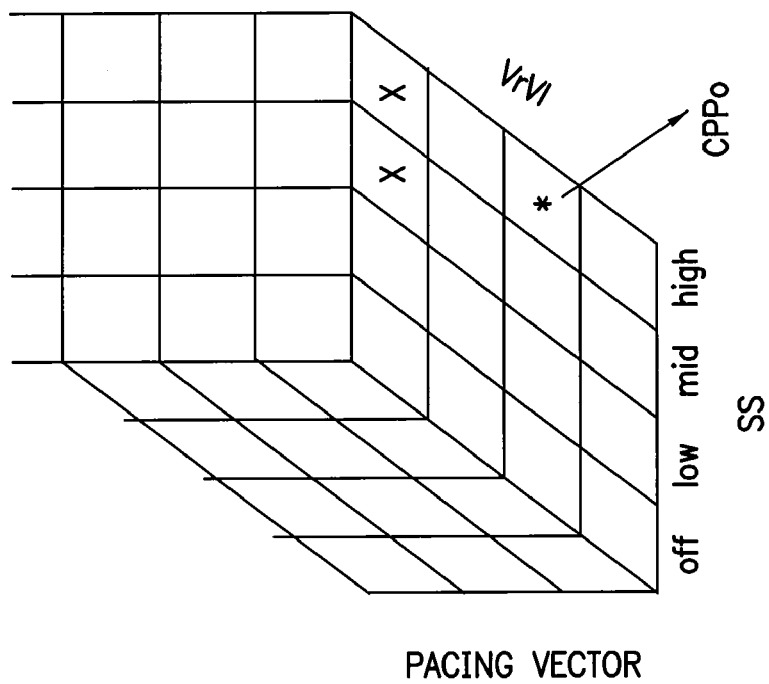
FIG. 5 depicts a three dimensional array/matrix (matrix optimization method) used for defining the optimal pacing parameters using a number of variables including pacing vector, stimulation strength and interval timing

Decisions with regard to which vectors are utilized and pacing stimulus strength may be based on tissue Doppler echocardiography data, pacing thresholds or both. Given the number of permutations of vectors and pacing modalities available (FIG. 5) with such systems, an interface between tissue Doppler echocardiography equipment and CRT device/programmer would expedite such programming (an example of which is described in co-pending application titled "METHOD AND APPARATUS FOR AUTOMATICALLY PROGRAMMING CRT DEVICES," U.S. patent application Ser. No. 10/779,162, the disclosure of which is hereby incorporated by reference). The determination of optimal settings can be decided upon in a hierarchal fashion with such an interface. By way of example, one can chose to evaluate optimal programming based on changes in AV delay (AVD), timing between RV and LV leads (VrVI), and pacing vector. One could use the absence of DS or even stimulus strength (SS) as a parameter in such an optimization algorithm (in an effort to balance the benefit of decreased energy expenditure (battery longevity) and optimal pacing configuration). The number of permutations that may be tried (e.g. VrVI×SS×AVD) may be significant and as such a means of automatically defining the optimal pacing parameters that considers the multiple variables described herein is ideal.

A three dimensional array or 3D matrix optimization method can be employed for such analysis. An alternate means for analyzing the effect of programming any of a number of permutations of the variables described herein on cardiac performance are within the scope and spirit of this invention and the matrix optimization method is exemplary. The analysis may use external input data via an interface (e.g. tissue Doppler data) or internal data such as multipolar electrogram disparity characteristics and/or impedance signals. The input data used will be evaluated until the optimal cardiac performance parameter is identified (CPPo in FIG. 5). This CPPo will relate to the optimal pacing modality (e.g. high SS, VrVI=20 ms, LV bipolar pacing vector). The internal system will allow optimal system operation in a dynamic fashion as part of a closed loop system. Certain pacing modalities (e.g. high energy pacing, non-excitatory stimulation (Impulse Dynamics)) can be utilized under specific conditions (an example of which is described in co-pending application titled "OPTIMIZATION OF IMPEDANCE SIGNALS USED FOR CLOSED LOOP PROGRAMMING OF CARDIAC RESYNCHRONIZATION DEVICES," U.S. patent application Ser. No. 10/860,990, the disclosure of which is hereby incorporated by reference). Indeed, even higher energy LV pacing using a conventional device with an electrode combination using an LV lead to RV coil (anodal stimulation) has been demonstrated to reduce dysynchrony and alter surface ECG morphology. As such, in specific patients, it may be appropriate to use higher energy pacing and cause anodal stimulation. Such a patient would have a pacing configuration that incorporates anodal stimulation as one of the initial programmed parameters, unless diaphragm stimulation was present. Specific combinations of pacing parameters that have been found to be disadvantageous (e.g. dysynchronous, previously caused DS) may be eliminated (X in FIG. 5) from the matrix. In a preferred embodiment, the system can even deactivate higher energy pacing once battery elective replacement indicators are reached.

In a preferred embodiment, the algorithms described herein can be implemented intra-operatively using the device, programmer and/or program stimulator as part of a separate apparatus. Specific morphologic changes in evoked potential and/or electrogram signals may indicate sub-clinical DS (not otherwise appreciated) and guide lead placement and device programming.

The present invention is not intended to be limited to the embodiments shown and described herein but is to be accorded the widest scope consistent with the principles and novel features disclosed herein.

What is claimed is:

1. A method for detecting diaphragmatic stimulation comprising:
    delivering a stimulation pulse to a patient's heart;
    sensing an electrogram signal of the heart resulting from the stimulation pulse; and
    analyzing the sensed electrogram signal of the heart to detect diaphragmatic stimulation that is induced by the stimulation pulse delivered to the heart.

2. The method of claim 1 and further comprising changing an operating parameter in response to detection of diaphragmatic stimulation.

3. The method of claim 2 wherein changing an operating parameter comprises changing a stimulation pulse parameter.

4. The method of claim 3 wherein the stimulation pulse parameter comprises at least one of amplitude and pulse width.

5. The method of claim 2 wherein changing an operating parameter comprises changing a pacing configuration.

6. The method of claim 2 wherein changing an operating parameter comprises terminating delivery of stimulation pulses to a portion of the heart.

7. The method of claim 1 wherein delivering comprises delivering a left ventricular stimulation pulse.

8. The method of claim 1 wherein detecting diaphragmatic stimulation comprises comparing the electrogram signal of the heart with a template.

9. The method of claim 1 wherein detecting diaphragmatic stimulation comprises processing the electrogram signal of the heart to obtain a measured value, and comparing the measured value with a stored value.

10. A system for detecting diaphragmatic stimulation comprising:
    means for delivering a stimulation pulse to a patient's heart;
    means for sensing an evoked response electrical potential signal of the heart resulting from the stimulation pulse; and
    means for detecting diaphragmatic stimulation that is induced by the stimulation pulse delivered to the heart, based on the sensed evoked response electrical potential signal of the heart.

11. The system of claim 10 and further comprising means for changing an operating parameter in response to detection of diaphragmatic stimulation.

12. The system of claim 11 wherein the means for changing an operating parameter comprises means for changing a stimulation pulse parameter.

13. The system of claim 12 wherein the stimulation pulse parameter comprises at least one of amplitude and pulse width.

14. The system of claim 11 wherein the means for changing an operating parameter comprises means for changing a pacing configuration.

15. The system of claim 11 wherein the means for changing an operating parameter comprises means for terminating delivery of stimulation pulses to a portion of the heart.

16. The system of claim 10 wherein the means for delivering comprises means for delivering a left ventricular stimulation pulse.

17. The system of claim 10 wherein the means for detecting diaphragmatic stimulation comprises means for comparing the evoked response electrical potential signal of the heart with a template.

18. The system of claim 10 wherein the means for detecting diaphragmatic stimulation comprises means for processing the evoked response electrical potential signal of the heart to obtain a measured value, and means for comparing the measured value with a stored value.

* * * * *